(12) United States Patent
Liénard et al.

(10) Patent No.: US 6,215,849 B1
(45) Date of Patent: Apr. 10, 2001

(54) METHOD FOR OBTAINING A DIGITIZED RADIOGRAPHIC PICTURE OF AN OBJECT

(75) Inventors: Jean Liénard, Clamart; Anne Marie Rougée, Palaiseau, both of (FR)

(73) Assignee: GE Medical Systems SA (FR)

( * ) Notice: Subject to any disclaimer, the term of this patent is extended or adjusted under 35 U.S.C. 154(b) by 0 days.

(21) Appl. No.: 09/232,982

(22) Filed: Jan. 19, 1999

(30) Foreign Application Priority Data

Jan. 22, 1998 (FR) .................................................. 98 00643

(51) Int. Cl.[7] ....................................................... H05G 1/60
(52) U.S. Cl. ............................................. 378/98.12; 378/62
(58) Field of Search .......................... 378/62, 98.2, 98.12

(56) References Cited

U.S. PATENT DOCUMENTS 4,613,983 * 9/1986 Yedid et al. ....................... 378/98.12

FOREIGN PATENT DOCUMENTS 4231583 3/1994 (DE).
2565053 11/1985 (FR).

* cited by examiner

*Primary Examiner*—David V. Bruce
(74) *Attorney, Agent, or Firm*—Jay L. Chaskin

(57) ABSTRACT

A digitized secondary image which promotes predetermined elements of interest of the object is created from each primary image, digital processing for two-dimensional mutual resetting of the secondary images is carried out per pair of consecutive images, for each current reset secondary image a region common to the said current image and to the following reset secondary image is defined which is bounded by the two respective median horizontal lines of the two reset secondary images, and the digitized overall radiographic picture is created from the upper region of the first reset secondary image of the succession, lying above the common region of this first image, from the lower region of the last reset secondary image of the succession, lying below the common region of this last image, and from the common regions of each pair of reset secondary images.

29 Claims, 3 Drawing Sheets

METHOD FOR OBTAINING A DIGITIZED RADIOGRAPHIC PICTURE OF AN OBJECT

BACKGROUND OF THE INVENTION

The invention relates to the obtaining of a digitized overall radiographic picture of an object from a succession of partially overlapping initial radiographic pictures taken from different points of view.

The invention applies advantageously, but without implying any limitation, to the pictures acquired in the course of an arteriography of the lower limbs, or in the course of a radiography of the spine from successive images acquired along the vertebral column.

Hardening, stenosis and blocking of the arteries of the lower limbs are detected during a vascular examination of all of the two limbs.

One conventional solution consists in employing an arteriophlebography drum which, on each of its faces, has a cassette of radiological film having a length of approximately 1.20 m. Exposing the patient to X-radiation therefore makes it possible to obtain an overall picture of the lower limbs directly. However, such a solution requires the use of bulky equipment.

Furthermore, a more recent solution consists in using successive films of smaller size (35×35) combined with a programmed advance table. The radiologist can then monitor the progress of the contrast product flowing through the blood vessels of the lower limbs, for example. The various images are then cut manually to avoid overlaps and are repasted manually to reconstruct an image with a total length of 1.20 m, allowing the leg to be viewed in its entirety.

Such a solution therefore requires the handling of films when the radiologist wishes to reconstruct a panoramic view of the legs.

The invention aims to provide a more satisfactory solution to the problem of obtaining an overall radiographic picture of an object from a succession of partially overlapping initial radiographic pictures taken from different points of view.

BRIEF SUMMARY OF THE INVENTION

An embodiment of the invention provides an automatic way, in a computer, of cutting and pasting digital pictures having partial overlap.

In this regard, the embodiment uses the partial overlap zones between the successive pictures to "digitally paste" the pictures in order to obtain the digitized overall picture of the object, in particular the leg.

An embodiment of the invention therefore proposes a method for obtaining a digitized overall radiographic picture of an object from a succession of partially overlapping initial or "primary" radiographic pictures taken from different points of view.

In an embodiment of this method, a digitized secondary image which promotes predetermined elements of interest of the object is created from each primary image or picture. Such a secondary image is, for example in an arteriography application, an image on which the predetermined elements of interest of the object appear, in this case the blood vessels. Such a secondary image may, for example, be obtained by taking the difference between an opacified image (primary image), after injection of a contrast product into the leg, and a so-called "mask" image, that is to say an image obtained without contrast product.

Digital processing for two-dimensional mutual resetting of the secondary images is then carried out per pair of consecutive images so as to obtain mutually reset digitized secondary images. This reset processing is carried out by promoting the predetermined elements of interest of the object and takes into account the motion of the picture acquisition system relative to the patient, for example the displacement step of the table, which may be known or unknown, and the depth of the various elements of interest (for example the blood vessels) inside the object (for example the leg).

For each current reset secondary image a region common to the said current image and to the following reset secondary image is then defined, this common region being bounded by the two respective median horizontal lines of the two reset secondary images. The digitized overall radiographic picture is then created from the upper region of the first reset secondary image of the succession of images taken, this upper region lying above the common region of this first image. The radiographic picture is also created from the lower region of the last reset secondary image of the succession, this lower region lying below the common region of this last image. Lastly, the overall radiographic picture is created from the common regions of each pair of reset secondary images.

According to one embodiment of the method, for each reset secondary image a common region is defined which includes an upper common zone and a lower common zone which respectively extend on either side of the median cut line of the said common region. The overall radiographic picture is then created by using, for each common region, the upper common zone of the common region of the current secondary image and the lower common zone of the common region of the following secondary image.

In other words, the cut line is defined as the trace lying in the middle of the region common to a pair of successive secondary images, a common region whose upper (or lower, respectively) transverse boundary corresponds to the median horizontal line (central line) of the first (or second, respectively) picture of the pair in question. The digital pasting is carried out by aligning and superimposing the cut line while keeping the section (upper common zone) lying above the cut line of the first picture of the pair in question and the section (lower common zone) lying below the cut line of the second picture of the pair in question.

However, when two cuts are assembled in this way, a picture is obtained whose transition is visible on the overall radiographic picture, because of the differences in intensity which are connected with the disparities of points of view, path and absorption of the X-rays giving rise to these pictures.

The embodiment of the invention thus very advantageously proposes digital pasting by "lap dissolve" allowing this problem to be solved. In other words, the final picture results from a progressive transition from one picture to the next, by fading the first and introducing the following one. The various cut lines are therefore invisible in the overall radiographic picture, the background then being continuous.

In other words, according to this advantageous variant of the embodiment of the invention, the overall radiographic picture is created by using, for each common region, a weighted sum of the logarithms of the grey levels of the respective upper and lower common zones of two consecutive reset secondary images.

In certain applications, in particular in arteriography, the acquisition of the primary images may include acquisition of primary images taken from different points of view, referred to as "moving images", and acquisition of at least one group of several consecutive primary images taken from the same point of view, referred to as "fixed images". The fixed secondary images corresponding to the fixed primary images are then created, and from these fixed secondary images, a resultant secondary image is created which is used, for the digital reset processing, with the last moving secondary image preceding the first fixed image of the said group, and with the first moving secondary image following the last fixed image of the said group.

The creation of the secondary image resulting from the fixed images advantageously comprises a search for maximum intensity between the corresponding pixels of the fixed secondary images.

In other words, the pictures acquired with fixed points of view, for example in order to fully opacify the underlying arterial network, are merged beforehand into a single picture which will be combined with the moving adjacent pictures of the series of pictures acquired.

The creation of each secondary image which promotes the predetermined elements of interest may comprise acquisition, for each take, of the primary image on which the elements of interest appear (opacified image) and a mask image on which the elements of interest do not appear (unopacified image), then subtraction of the primary image and the mask image.

Preliminary reset processing is then advantageously carried out between each primary image acquired and the corresponding mask image acquired, so as to prevent the appearance of artifacts due to movements by the patient.

When the mask image is not acquired per se, in particular when the displacement step of the table on which the patient is lying is not known in advance, low-pass filtering of the primary image is carried out so as to obtain a mask image.

When the predetermined displacement step of the table is known, the reset processing between the consecutive secondary images includes a search for coincidence between a predetermined central zone of the current image and the same central zone of the following image taking the displacement step into account.

However, in the case when the successive taking of the moving images is spaced by an a priori unknown displacement step, the displacement step is determined from the content of the secondary images by making a search for coincidence between two secondary images and preferably on reduced regions of these images, so as to speed up the calculations.

BRIEF DESCRIPTION OF THE DRAWINGS

Other advantages and characteristics of embodiments of the invention will become apparent on examining the description of an entirely non-limiting embodiment, and the appended drawings, in which.

DETAILED DESCRIPTION OF THE INVENTION

Figure 1:
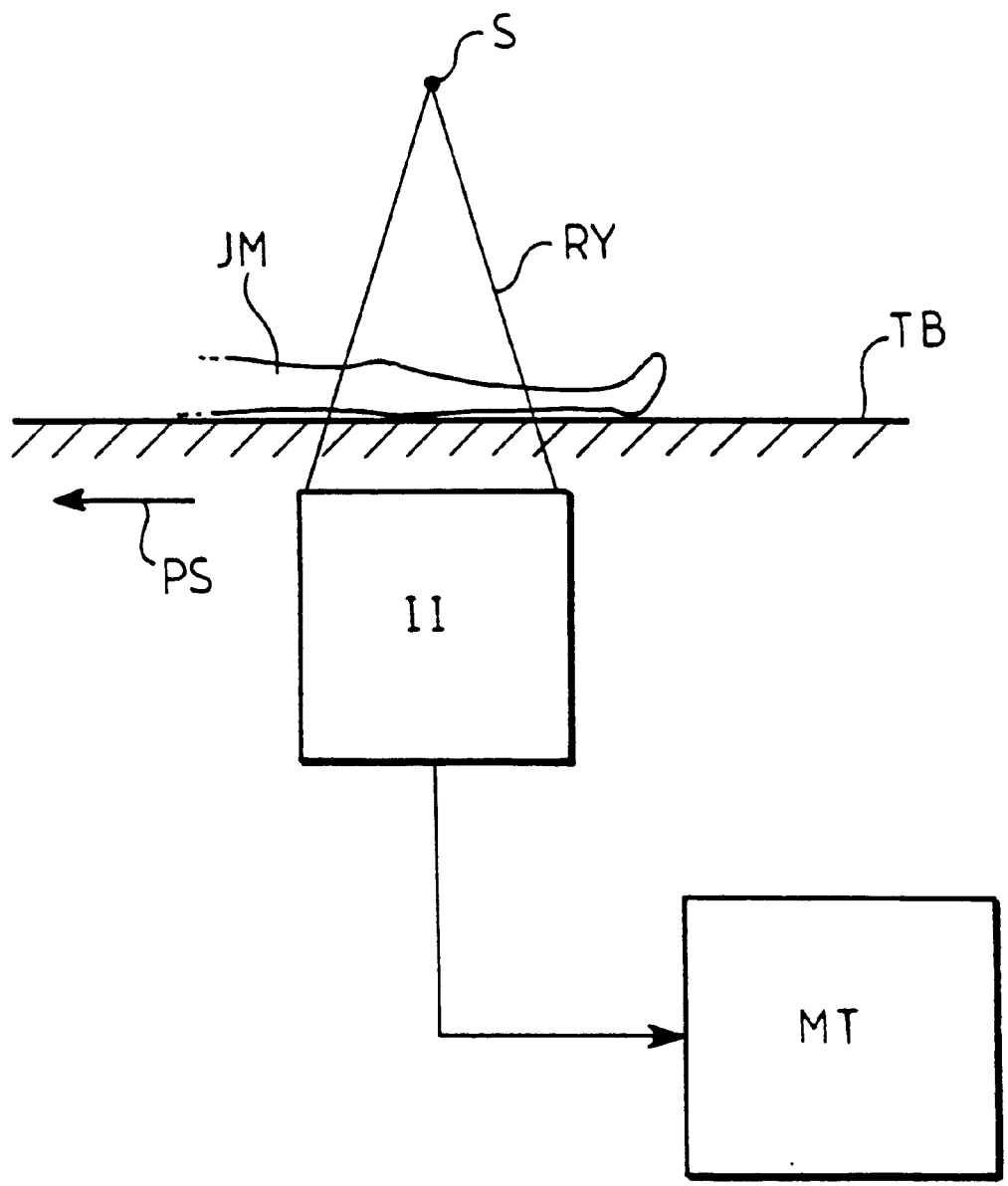
FIG. 1 very schematically illustrates a device for implementing an embodiment of the invention.

In FIG. 1, the reference TB denotes a table which can be moved horizontally with the predetermined displacement step PS. A patient's leg JM is resting on this table with a view to an arteriographic examination.

To this end, a source S which emits X-radiation and is referenced RY illuminates the leg JM and is received on the opposite side of the table TB by reception means which are known per se and, in particular, include an image intensifier 11 whose maximum field corresponds to 35×35 cm images.

Processing means MT essentially consisting of a computer and of a screen for viewing the images, are connected to this image intensifier 11.

In a first step of the method, a succession of images, termed mask images, which are respectively taken from different points of view and each correspond to a different position of the table, is acquired. It will therefore be assumed here that all the images acquired are images termed "moving" as opposed to images termed "fixed", whose significance will be discussed in detail below.

These mask images correspond to radiographic images taken without injecting contrast product into the blood vessels of the leg.

After this acquisition of the mask images, a contrast product is injected into the blood vessels of the patient's leg, then opacified images, termed primary images, are acquired from points of view respectively identical to those of the corresponding mask images.

The blood vessels appear on these primary images. This being the case, in order to promote the blood vessels in relation to the background of the radiographic picture, and thus to be able, as will be seen in more detail below, to reset the successive images in relation to these blood vessels, each mask image is subtracted from the corresponding primary image, so as to obtain an image termed secondary which promotes the predetermined elements of interest of the object, namely the blood vessels of the leg.

This being the case, this subtraction operation is preceded by automatic processing for resetting the mask on the primary image in order to avoid the appearance of artifacts due to movements by the patient. The picture reset processing is conventional processing which is well-known to the person skilled in the art. In general, it consists in preprocessing the pictures, in selecting a certain number of check points (which is referred to as landmarks), in estimating the distortion at each of these landmarks, in validating these landmarks, in interpolating the distortion for the entire picture, and in restoring the picture with correction.

More precisely, use may be made of a search for coincidence between pictures which are based on calculating a similarity criterion, making it possible to determine on each picture the lateral and longitudinal translation which best superimposes it on the picture before it.

A method for pneumatic resetting of pictures, using in particular a correlation factor, has been proposed in French patent No. 89 04 085 (corresponding to U.S. Pat. No. 5,048,103).

Resetting of pictures using a change of sign criterion is also known from the article by V. Leclerc and C. Benchinol entitled "recalage élastique d'images angiographiques" [elastic resetting of angiographic images], 11th Symposium on signal and image processing, Nice, Jun. 1–5, 1987, pages 487–489, Gretsi. The person skilled in the art may if required refer to these prior documents, whose content is for the purpose of information incorporated in that of the present description.

In general, optimum superimposition of two pictures gives the similarity criterion a maximum value, making it possible to deduce the X and Y shift of one picture relative to the other, and therefore correctly to subtract, pixel by pixel, the mask image and the primary image.

This being the case, the coincidence search using the similarity criterion is preferably carried out on a reduced region of the mask image and of the corresponding primary image. In this regard, a central region of each image will be taken, for example a rectangular region whose height and width take account of the circular shape of the pictures, as well as the possible presence of lateral collimators. A non-limiting example of these dimensions is, as regards the height, a dimension equal to one quarter of the size of the picture and, as regards the width, a dimension equal to the size of the picture reduced at most by the total width of the lateral collimators, and reduced at least by one twentieth of the picture size.

Once the series of digitized secondary images has been obtained, digital processing for two-dimensional mutual resetting of the secondary images is carried out by pairs of consecutive secondary images so as to obtain mutually reset digitized secondary images.

The reason for this is that, even though the displacement step of the table is known in the example being described here, the depth of the various blood vessels in the leg is not accurately known. Consequently, in view of the conical projection of the blood vessels in the various images, their displacement relative to their position in the preceding picture is not accurately known. It is therefore appropriate to determine this X and Y shift accurately so as to be able to digitally paste the pictures in order to obtain almost perfect continuity of the blood vessels from one picture to another.

This automatic reset processing is carried out in a manner similar to that described above for resetting the masks in relation to the opacified pictures. More precisely, a coincidence search is carried out, using the similarity criterion, by moving the central region of the current picture into the central region of the following picture, shifted by the displacement step of the table, with in addition a shift tolerance taking account of the maximum thickness of the object, in this case the leg. In this way, not only the displacement of the table, but also the possible difference in depth of the element of interest in the leg from one picture to another are taken into account.

By way of example, a region having a height equal to one quarter of the size of the picture (for example 10 cm in height) will be chosen as the central region. If the successive taking of the various images is spaced by 6 cm (which is assumed here to be the predetermined displacement step of the table), the search region chosen in the current picture will be the central region of this current picture, shifted by 6 cm, plus or minus 2 cm for example, to take into account the unknown parameter relating to the depth of the vessel in the leg.

In order to speed up the calculations, the automatic correspondence of the vascularized zones, based on optimizing the similarity criterion between the two central regions which are taken from two successive secondary images, is obtained using a multiresolution approach. More precisely, a search is firstly made for the position of the maximum of the similarity criterion by displacing the central region of the current picture into the search region of the following picture, with a search increment fixed at 4 pixels by row and by column. Secondly, the central region of the current picture is centered at the point corresponding to the position of the maximum of the similarity criterion, this position being obtained in the previous phase, and is moved over the eight neighboring points with a search increment equal to 2 pixels in order to determine a new maximum of the similarity criterion at a new point. Lastly, a third search phase is carried out by centering the central region on the new point obtained in the preceding step, and is moved over the eight neighboring points of this new point, with an increment of 1 pixel in order to determine the final position of the maximum of the similarity criterion and thus obtain the X and Y shift of the following image in relation to the preceding image.

Figure 2:
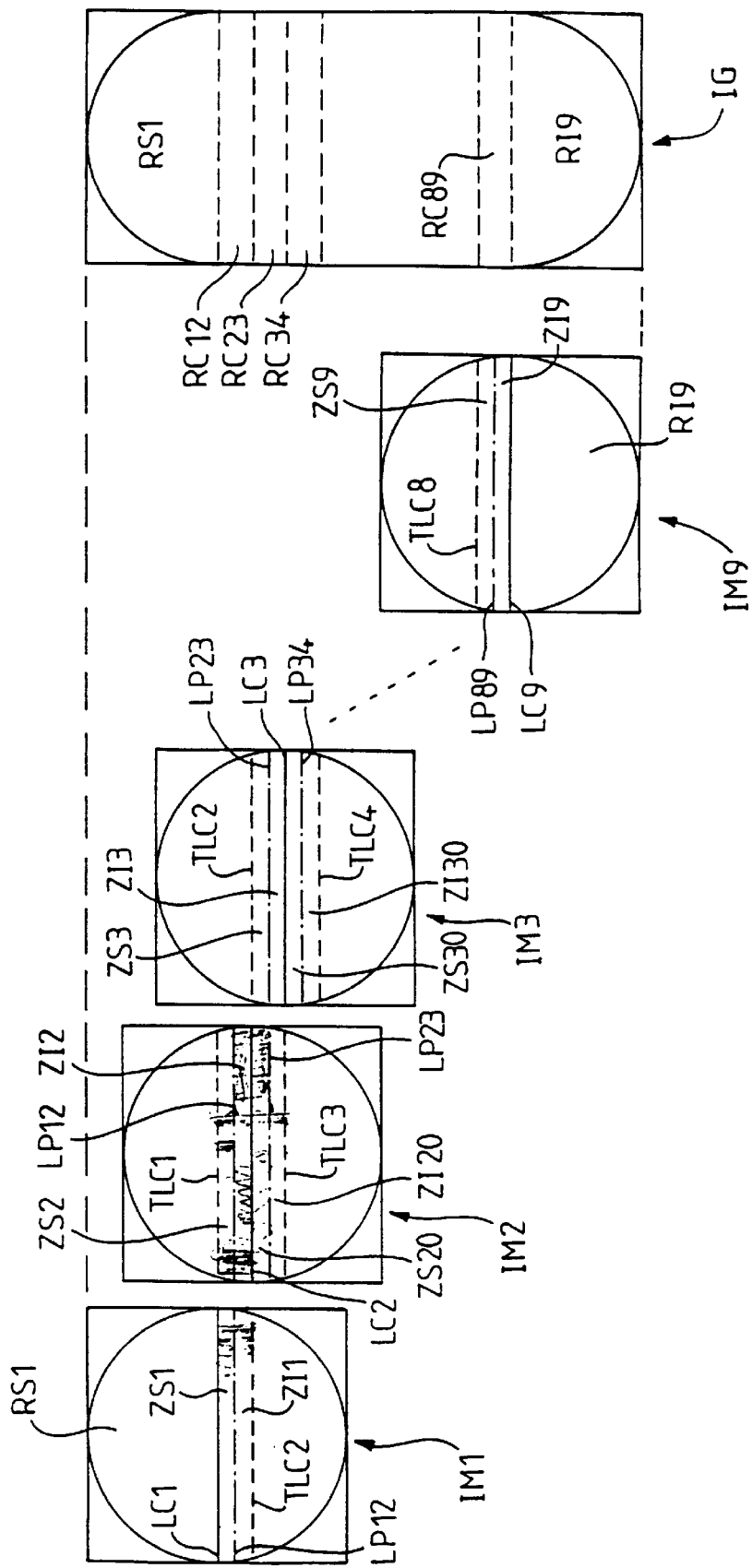
FIG. 2 very schematically illustrates a series of images for obtaining an overall picture by a method in an embodiment of the invention.

At the end of this digital shift processing, a series of reset secondary images is obtained, which has been referenced in FIG. 2 with the references IM1–IM9. It is in fact assumed here in this example, for the sake of simplicity, that nine moving images have been acquired in order to obtain the overall picture IG.

For each current secondary image IMi, a common region is defined which is bounded by the median horizontal line LCi of the current picture (central line of the picture) and the plot TLCj of the median horizontal line LCj of the following picture IMj.

A cut line LPij dividing this common region into two equal zones, namely an upper common zone ZSi and a lower common zone ZIi, is then defined.

The two-dimensional resetting of the secondary images results in alignment of the cut lines of two consecutive images, which has been represented in FIG. 2.

Next, in the memory of the processing means MT, the overall picture IG is created by using the upper region RS1 of the first reset secondary image IM1 of the succession, the lower region R19 of the last secondary image IM9 of the succession, and the common regions RC12, RC23, RC34–RC89 of each pair of reset secondary images.

As regards the common regions which are used, one solution might consist in simply using the upper common zone of the current picture and the lower common zone of the following picture. Thus, for example, for the common region RC23, which region is common to the pictures IM2 and IM3, successive use may be made of the pixels of the upper common zone ZS20 and then the pixels of the lower common zone ZI20.

This being the case, such a solution may lead to obtaining an overall picture inside which the various cut lines are visible.

In order to overcome this drawback, it is preferable to carry out a lap dissolve operation. More precisely, for each common region, a weighted sum of the logarithms of the grey levels of the respective upper and lower common zones of two consecutive reset secondary images is used.

In other words, for example for the common region RC23, for the pixels lying level with the central line LC2, 100% of the level of the pixels of the zone ZS20 will be used and 0% of the levels of the pixels of the zone ZS3 will be used.

As regards the pixels lying on the cut line LP23, their level will be equal to 50% of the levels of the pixels of the line LP23 of the picture IM2 and to 50% of the levels of the pixels of the line LP23 of the picture IM3.

Lastly, the pixels lying on the line LC3 will have levels equal to 100% of the pixels of the line LC3 of the picture IM3 and to 0% of the pixels of the line TLC3 of the picture IM2.

This lap dissolve operation, corresponding to a weighted sum of the logarithms of the grey levels, followed by exponentiation, corresponds in X-radiology to weighted addition of the densitometric thicknesses.

Further to the moving images taken from different points of view, certain applications may require the acquisition of fixed images, that is to say successive images taken at a same point of view, that is to say at the same position of the table TB.

Figure 3:
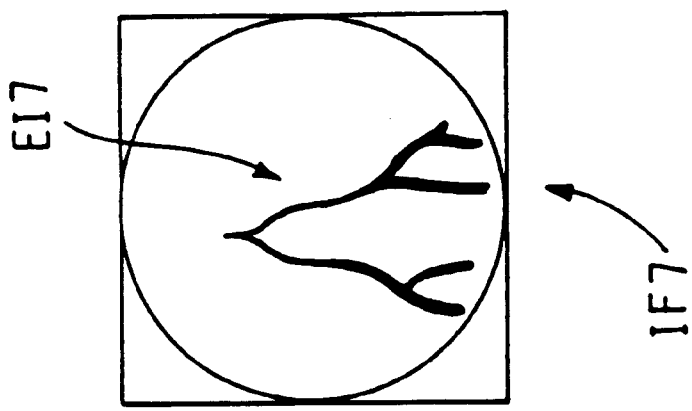
FIG. 3 very schematically illustrates the obtaining of three fixed images acquired during an arteriography.
Figure 3:
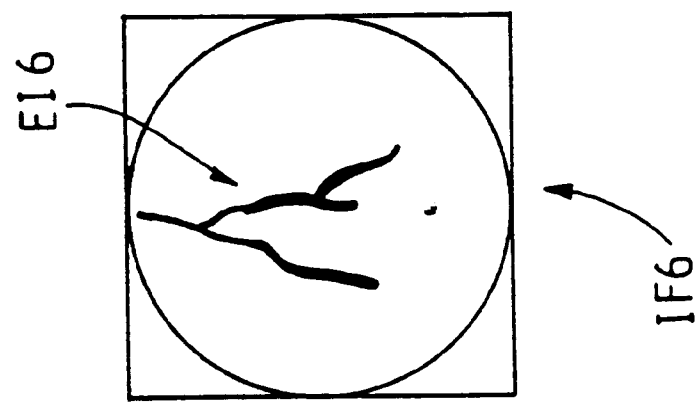
Figure 3:
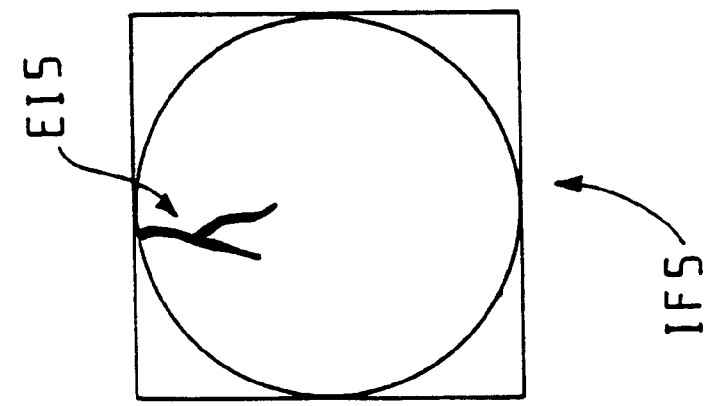

This makes it arteriographic possible, examinations, to in particular in let the contrast product propagate so as to have a more accurate view of the blood network. This is the case, for example, of the fixed images IF5, IF6 and IF7 which are represented in FIG. 3. It will be noted that the upper part EI5 of the blood network appears on the picture IF5, whereas on the picture IF6, the upper part still remains but with lower contrast than the median part E16 of the blood network, while on image IF7, the upper part of the blood network has disappeared and the lower part E17 has a higher contrast than the median part.

According to the invention, these three images are digitally merged so as to obtain a single resultant image which will be used for the resetting relative to the moving image before the image IF5 and relative to the moving image following the image IF7. In this regard, this resultant secondary image is created by a search for minimum intensity between the corresponding pixels of the fixed secondary images. In other words, a search is made for the contrast maximum in each fixed image, and these strongly contrasted parts will be used for creating the resultant secondary image.

When no indication is given about the movement of the patient relative to the image intensifier, the step of the table has to be determined from the content of the pictures. The inter-picture similarity criterion is then calculated on the primary pictures, reduced beforehand to one quarter of their dimensions in order to speed up the calculations, in order to determine on each picture the lateral and longitudinal translation which best superimposes it on the picture before it. optimum superimposition of the two pictures gives the similarity criteria a maximum value, which makes it possible to determine, in particular, the Y displacement and therefore the displacement step between the two consecutive pictures. This being the case, in this context the search for this maximum is carried out by successive displacements of limited regions of the pictures. In actual fact, the similarity should relate to regions which only contain anatomical structures, to the exclusion of fixed mechanical parts of the imaging system, such as the leaded collimators, which risk vitiating the measurement of the criteria. The measurement regions need to be wide enough to cover the various organs whose edges assist the measurement. Finally, the measurement regions should be limited in size in order to reduce the calculation time.

By way of indication, rectangular regions may be taken whose height and width take into account the circular shape of the pictures as well as the possible presence of lateral collimators. In that case, a height equal to one quarter of the picture size and a width equal to the picture size, reduced at most by the size width of the lateral collimators and reduced at least by one twentieth of the picture size, may also be chosen for these rectangular regions.

The embodiments of the invention therefore makes it possible to obtain an overall picture in which the main vessels or the bones (in the case of an orthopedic bone examination, for example) are continuous over the entire range examined, in which the cut lines are invisible (continuous background) and in which the contrast is highest for the elements of interest, in particular the vascular structures.

Various modifications in structure and/or function and/or steps may be made by one skilled in the art without departing from the scope and extent to the invention.

What is claimed is:

1. A method for obtaining a digitized overall radiographic picture of an object from a succession of partially overlapping primary radiographic pictures taken from different points of view comprising the steps of:
   (a) creating from each primary image a digitized secondary image which promotes predetermined elements of interest of the object;
   (b) carrying out digital processing for two-dimensional mutual resetting of the secondary images per pair of consecutive images so as to obtain mutually reset digitized secondary images;
   (c) for each current reset secondary image a region common to the current image and to the following reset secondary image which is bounded by two respective median horizontal lines of the two reset secondary images; and
   (d) creating a the digitized overall radiographic picture is from the upper region of the first reset secondary image of the succession, lying above the common region of the first image, from the lower region of the last reset secondary image of the succession, lying below the common region of the last image, and from the common regions of each pair of reset secondary images.

2. The method according to claim 1 wherein the common region of each reset secondary image includes an upper common zone and a lower common zone which respectively extend on either side of the median cut line of the common region, and the overall radiographic picture is created by using, for each common region, the upper common zone of the common region of the current secondary image and the lower common zone of the common region of the following secondary image.

3. The method according to claim 1 wherein the common region of each reset secondary image includes an upper common zone and a lower common zone which respectively extend on either side of the median cut line of the common region, and the overall radiographic picture is created by using, for each common region, a weighted sum of the logarithms of the grey levels of the respective upper of two consecutive reset secondary images.

4. The method according to claim 1 wherein when the acquisition of the primary images includes acquisition of primary images taken from different points of view, referred to as moving images, and at least one group of several consecutive primary images taken from the same point of view, referred to as fixed images, the fixed secondary images corresponding to the fixed primary images are created, and from these fixed secondary images, a resultant secondary image is created which is used, for the digital reset processing, with the last moving secondary image preceding the first fixed image of the group, and with the first moving secondary image following the last fixed image of the group.

5. The method according to claim 2 wherein when the acquisition of the primary images includes acquisition of primary images taken from different points of view, referred to as moving images, and at least one group of several consecutive primary images taken from the same point of view, referred to as fixed images, the fixed secondary images corresponding to the fixed primary images are created, and from these fixed secondary images, a resultant secondary image is created which is used, for the digital reset processing, with the last moving secondary image preceding the first fixed image of the group, and with the first moving secondary image following the last fixed image of the group.

6. The method according to claim 3 wherein when the acquisition of the primary images includes acquisition of primary images taken from different points of view, referred to as moving images, and at least one group of several consecutive primary images taken from the same point of view, referred to as fixed images, the fixed secondary images corresponding to the fixed primary images are created, and from these fixed secondary images, a resultant secondary image is created which is used, for the digital reset processing, with the last moving secondary image preceding the first fixed image of the group, and with the first moving secondary image following the last fixed image of the group.

7. The method according to claim 4 wherein when the acquisition of the primary images includes acquisition of primary images taken from different points of view, referred to as moving images, and at least one group of several consecutive primary images taken from the same point of view, referred to as fixed images, the fixed secondary images corresponding to the fixed primary images are created, and from these fixed secondary images, a resultant secondary image is created which is used, for the digital reset processing, with the last moving secondary image preceding the first fixed image of the group, and with the first moving secondary image following the last fixed image of the group.

8. Method according to claim 4 wherein the creation of the resultant secondary image comprises a search for maximum intensity between the corresponding pixels of the fixed secondary images.

9. Method according to claim 5 wherein the creation of the resultant secondary image comprises a search for maximum intensity between the corresponding pixels of the fixed secondary images.

10. Method according to claim 6 wherein the creation of the resultant secondary image comprises a search for maximum intensity between the corresponding pixels of the fixed secondary images.

11. Method according to claim 7 wherein the creation of the resultant secondary image comprises a search for maximum intensity between the corresponding pixels of the fixed secondary images.

12. The method according claim 1 wherein the creation of each image which promotes the predetermined elements of interest comprises acquisition, for each take, of the primary image on which the elements of interest appear and a mask image on which the elements of interest do not appear, then subtraction of the primary image and the mask image.

13. The method according claim 2 wherein the creation of each image which promotes the predetermined elements of interest comprises acquisition, for each take, of the primary image on which the elements of interest appear and a mask image on which the elements of interest do not appear, then subtraction of the primary image and the mask image.

14. The method according claim 3 wherein the creation of each image which promotes the predetermined elements of interest comprises acquisition, for each take, of the primary image on which the elements of interest appear and a mask image on which the elements of interest do not appear, then subtraction of the primary image and the mask image.

15. The method according claim 4 wherein the creation of each image which promotes the predetermined elements of interest comprises acquisition, for each take, of the primary image on which the elements of interest appear and a mask image on which the elements of interest do not appear, then subtraction of the primary image and the mask image.

16. The method according claim 5 wherein the creation of each image which promotes the predetermined elements of interest comprises acquisition, for each take, of the primary image on which the elements of interest appear and a mask image on which the elements of interest do not appear, then subtraction of the primary image and the mask image.

17. The method according claim 6 wherein the creation of each image which promotes the predetermined elements of interest comprises acquisition, for each take, of the primary image on which the elements of interest appear and a mask image on which the elements of interest do not appear, then subtraction of the primary image and the mask image.

18. The method according claim 7 wherein the creation of each image which promotes the predetermined elements of interest comprises acquisition, for each take, of the primary image on which the elements of interest appear and a mask image on which the elements of interest do not appear, then subtraction of the primary image and the mask image.

19. The method according claim 8 wherein the creation of each image which promotes the predetermined elements of interest comprises acquisition, for each take, of the primary image on which the elements of interest appear and a mask image on which the elements of interest do not appear, then subtraction of the primary image and the mask image.

20. The method according claim 9 wherein the creation of each image which promotes the predetermined elements of interest comprises acquisition, for each take, of the primary image on which the elements of interest appear and a mask image on which the elements of interest do not appear, then subtraction of the primary image and the mask image.

21. The method according claim 10 wherein the creation of each image which promotes the predetermined elements of interest comprises acquisition, for each take, of the primary image on which the elements of interest appear and a mask image on which the elements of interest do not appear, then subtraction of the primary image and the mask image.

22. The method according claim 11 wherein the creation of each image which promotes the predetermined elements of interest comprises acquisition, for each take, of the primary image on which the elements of interest appear and a mask image on which the elements of interest do not appear, then subtraction of the primary image and the mask image.

23. The method according to claim 8 wherein preliminary reset processing is carried out between each primary image acquired and the corresponding mask image acquired.

24. The method according to claim 5 wherein preliminary reset processing is carried out between each primary image acquired and the corresponding mask image acquired.

25. The method according to claim 6 wherein preliminary reset processing is carried out between each primary image acquired and the corresponding mask image acquired.

26. The method according to claim 7 wherein preliminary reset processing is carried out between each primary image acquired and the corresponding mask image acquired.

27. The method according to claim 1 wherein the creation of each secondary image which promotes the predetermined elements of interest comprises acquisition, for each take, of the primary image on which the elements of interest appear, and low-pass filtering of the primary image so as to obtain a mask image, then subtraction of the primary image and the mask image.

28. The method according to claim 1 wherein the successive taking of the moving images is spaced by a predetermined displacement step, and the reset processing between the consecutive secondary images includes a search for coincidence between a predetermined central zone of the current image and the same central zone of the following image taking the displacement step into account.

29. The method according to claim 1 wherein when the successive taking of the moving images is spaced by an a priori unknown displacement step, the displacement step is determined from the content of the secondary images by making a search for coincidence between two secondary images on reduced regions of these images.

* * * * *